United States Patent
Bucks et al.

(10) Patent No.: US 6,277,364 B1
(45) Date of Patent: Aug. 21, 2001

(54) POLYURETHANES AS TOPICAL SKIN PROTECTANTS

(75) Inventors: Daniel A. W. Bucks, Millbrae; Albert M Dorsky, Palo Alto; Sui Yuen Eddie Hou, Foster City, all of CA (US)

(73) Assignee: Bertek Pharmaceuticals, Inc., Foster City, CA (US)

( * ) Notice: Subject to any disclaimer, the term of this patent is extended or adjusted under 35 U.S.C. 154(b) by 0 days.

(21) Appl. No.: 09/169,208

(22) Filed: Oct. 9, 1998

(51) Int. Cl.$^7$ .................................................. A61K 31/74
(52) U.S. Cl. ..................... 424/78.03; 424/401; 424/45; 514/938; 514/944
(58) Field of Search ................. 424/78.03, 401, 424/45; 514/772.3, 944, 938, 969

(56) References Cited

U.S. PATENT DOCUMENTS

| | | | |
|---|---|---|---|
| 2,698,824 | 1/1955 | Morgulis | 167/90 |
| 3,888,995 | 6/1975 | Katz et al. | 424/358 |
| 4,079,028 | 3/1978 | Emmons et al. | 260/29.6 |
| 4,155,892 | 5/1979 | Emmons et al. | 260/29.2 |
| 4,255,550 | 3/1981 | Gould | 528/44 |
| 4,913,897 | 4/1990 | Chvapil et al. | 424/59 |
| 4,962,178 | 10/1990 | Harisiades | 528/33 |
| 4,971,800 | 11/1990 | Chess et al. | 424/449 |
| 5,000,955 | 3/1991 | Gould et al. | 424/409 |
| 5,019,604 | 5/1991 | Lemole | 523/105 |
| 5,045,317 | 9/1991 | Chess et al. | 424/401 |
| 5,051,260 | 9/1991 | Chess et al. . | |
| 5,126,136 | 6/1992 | Merat et al. | 424/401 |
| 5,192,536 | 3/1993 | Huprich | 424/78.08 |
| 5,286,787 | 2/1994 | Podola et al. | 524/773 |
| 5,370,876 | 12/1994 | Noll et al. | 424/407 |
| 5,686,065 | 11/1997 | Haney | 424/59 |
| 5,688,498 | 11/1997 | Huprich et al. | 427/78.02 |
| 5,707,612 * | 1/1998 | Zofchak et al. | 424/78.03 |
| 5,807,957 * | 9/1998 | Samour et al. | 424/78.03 |
| 5,837,274 | 11/1998 | Shick et al. | 424/406 |
| 5,942,239 | 8/1999 | Huprich et al. . | |

FOREIGN PATENT DOCUMENTS

WO 93/21904   11/1993   (WO) .

OTHER PUBLICATIONS

Renova (tretinoin emollient cream) 0.05%, "Study Conclusions" Ortho Pharmaceutical Corporation (1996).

"See the Renova (tretinoin emolient cream) 0.05% difference" Ortho Pharmaceutical Corporation (1996).

Sanders, J.H. and Frisch, K. C., "Polyurethanes Chemistry and Technology", *Interscience Publishers*, Part I Chemistry, pp. 65–67 (1962).

* cited by examiner

*Primary Examiner*—Thurman K. Page
(74) *Attorney, Agent, or Firm*—Cooley Godward LLP

(57) ABSTRACT

Polyurethane compositions for the protection of skin from material that is harmful to the skin or substances that are capable of penetrating the skin, are described.

21 Claims, No Drawings

POLYURETHANES AS TOPICAL SKIN PROTECTANTS

TECHNICAL FIELD

This invention relates to the protection of skin from material that is harmful to the skin or substances that are capable of penetrating the skin. In particular, the invention relates to the use of polyurethanes for such protection.

BACKGROUND

The outer skin layer (epidermis) forms a natural barrier to harmful substances from entering the body from the outside world. However, both hydrophilic and hydrophobic substances, including substances harmful to the body, are capable of penetrating across the stratum corneum layer into the viable skin tissues. Additionally, when the skin is compromised by cuts, abrasions, rashes, and the like, infectious agents such as viruses or bacteria may more readily enter the body. Finally, the skin may itself be harmed by commonly used noxious agents, for example toxic chemicals used in the laboratory, in industry, and at home.

One method commonly used to protect skin against harmful substances is, of course, the wearing of latex or rubber gloves. However, in general gloves are uncomfortable to wear for extended periods of time because of perspiration build-up, they reduce tactile sensitivity, and gloves are themselves quite susceptible to tearing, formation of pinholes, etc., with the consequent breakdown of protection.

The foregoing discussion is addressed largely to the protection of the hands, but can equally apply to other areas of the body, in particular the face, which is another area for which protection is often sought. The conventional mode of protection for the face is a mask, for example a plastic face mask. However, wearing a mask is uncomfortable because of perspiration build-up, and tends to diminish clarity and scope of vision. There are also occasions when the whole body may need protection from exposure to harmful substances, and in these situations protective body suits are worn. Such body suits incorporate all of the disadvantages of gloves or face mask mentioned above.

It would therefore be advantageous to have a means of protecting skin from harmful substances that does not require the use of gloves, face masks, or whole body suits. Such a means of protection should guard against toxic substances harmful to the skin itself, and substances capable of penetrating the skin barrier, such as viruses, bacteria, parasites, poisonous gases, toxic agents such as pesticides and herbicides, agents used as chemical weapons, for example mustard gases or neurotoxic agents, chemicals, and the like. The skin protectant should be simple and uncomplicated to apply, and not easily removed by water and aqueous environments. Greater skin protection would be provided if the protecting agent not only formed a barrier on the skin surface, but also was absorbed into the outer layer of the skin, i.e. the stratum corneum itself. Its presence in the stratum corneum would enhance efficiency as well as duration of action, in part due to the increased resistance to removal by friction or wiping. In this manner, a durable barrier would be formed that is not easily removed inadvertently or by solvents. Clearly this would be desirable, because in this manner the protective barrier function of the stratum cornea itself would be enhanced, and the barrier would not merely form a thin layer above the skin surface.

RELEVANT LITERATURE

Polyurethane hydrogels are disclosed for uses including cosmetic, biological and medical applications, such as carrier and delivery systems for pharmacologically active agents in Chvapil, et al., U.S. Pat. No. 4,913,897 and Gould, et al., U.S. Pat. No. 5,000,955, including the use of hydrogel solutions to form hydrophilic protective films on the skin.

Chess, et al., in U.S. Pat. Nos. 4,971,800, 5,045,317, and 5,051,260, disclose compositions comprising hydroxy-terminated polyurethanes that are useful for enhancing the cutaneous penetration of topically or transdermally delivered pharmacologically active agents. In Quigley, et al., WO 93/21904, assigned to the assignee of the present application, it is disclosed that such polyurethanes are also capable of increasing deposition of retinoic acid and sunscreens on and in the skin.

SUMMARY OF THE INVENTION

One aspect of the present invention relates to a topical composition for protecting the skin of a mammal, comprising: a polyurethane of Formula (I):

$$H\text{-}[\text{-}(YR)_m\text{--}OC(O)NH\text{--}X\text{--}NHC(O)]_n\text{--}(YR)_m\text{--}OC(O)NH\text{--}X\text{--}NHC(O)O\text{--}(RY)_m\text{--}\text{--}[C(O)NH\text{--}X\text{--}NHC(O)O\text{--}(RY)_m\text{-}]_{n'}\text{--}H \quad (I)$$

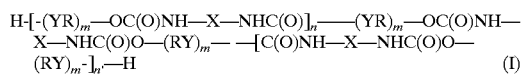

wherein:
X is an alkylene or alkenylene radical containing from 1 to about 20 carbon atoms, or a cycloalkylene or cycloalkenylene radical containing from about 5 to 20 carbon atoms, or a mononuclear or fused ring arylene radical containing from about 6 to about 10 carbon atoms, unsubstituted or substituted with one or more lower alkyl, lower alkoxy, lower alkoxy-substituted lower alkyl, nitro or amino groups or halogen atoms;

Y is oxygen, sulfur or $-NR_1-$, where R' is hydrogen or lower alkyl;

R is the same or different, and is chosen from alkylene, alkenylene, $-SiR^2R^3-$, and $-CR^2R^3-NR^4-CR^2R^3-$, wherein $R^2$, $R^3$ and $R^4$ are independently hydrogen or lower alkyl;

m is an integer selected to provide a (YR) moiety having a molecular weight of from about 40 to about 10,000; and n and n' are the same or a different integer from 0–30 inclusive, correlated with m so as to provide a polyurethane compound having a molecular weight of up to about 200,000; and optionally a diluent; in the absence of a pharmacologically active agent.

Another aspect of the invention relates to a method for protecting the skin of a mammal, comprised of applying an effective amount of a polyurethane of Formula (I), optionally combined with a diluent, to the skin of a mammal.

Yet another aspect of the invention relates to an article of manufacture, comprising a topical composition comprising a polyurethane of Formula (I), and optionally, a diluent in combination with labeling instructions for application of said topical composition for the protection of skin.

DESCRIPTION OF SPECIFIC EMBODIMENTS

Definitions

As used herein:

"Alkyl" means a branched or unbranched saturated monovalent hydrocarbon radical containing 1 to 12 carbon atoms, such as methyl, ethyl, propyl, isopropyl, tert-butyl, butyl, n-hexyl, dodecyl, and the like, unless otherwise indicated. "Lower alkyl" means a branched or unbranched saturated monovalent hydrocarbon radical containing 1 to 6 carbon atoms, such as methyl, ethyl, propyl, isopropyl, tert-butyl, butyl, n-hexyl and the like, unless otherwise indicated.

"Lower alkoxy" means the group —O—(lower alkyl) wherein lower alkyl is as herein defined.

"Alkylene" means a branched or unbranched saturated divalent hydrocarbon radical containing about 1 to 20 carbon atoms, such as methylene, trimethylene, dimethyltrimethylene, ethylene, 1,2-propylene, 1,4-butylene, 1,3-butylene, 1,5-pentylene, 1,3-pentylene, 1,6-hexylene, 1,12-docecylene, and the like. Similarly, "cycloalkylene" means a saturated divalent hydrocarbon radical containg from about 5 to 20 carbon atoms, such as cyclopentylene and cyclohexylene.

"Alkenylene" means a branched or unbranched unsaturated divalent hydrocarbon radical containing about 1 to 3 double bonds and about 2 to 20 carbon atoms, such as ethene, 1-propene, 1-butene, 3-methylbut-1-ene, 1-pentene, 2-methylpent-1-ene, 1-hexene, 1-docecene, and the like. Similarly, "cycloalkenylene" means an unsaturated divalent hydrocarbon radical containing from about 5 to 20 carbon atoms such as cyclohexenylene.

"Halo" or "halogen" means fluoro, chloro, bromo, or iodo.

The term "aryl" or "arylene" refers to a monovalent unsaturated aromatic carbocyclic radical having a mononuclear or single ring (e.g., phenyl) or two fused rings (e.g., naphthyl, biphenyl, indanyl, 1,2,3,4-tetrahydronaphthyl, benzocycloheptane), containing from about 6 to about 10 carbon atoms, and which can optionally be mono-, di- or tri-substituted, independently, with —OH, —COOH, lower alkyl, lower alkoxy, halo, nitro, amino, alkylamino, dialkylamino, trifluoromethyl and/or cyano.

"Optional" or "optionally" means that the subsequently described event or circumstance may or may not occur, and that the description includes instances where said event or circumstance occurs and instances in which it does not. For example, "optionally substituted phenyl" or "optionally substituted naphthyl" means that the phenyl or naphthyl may or may not be mono-, di- or tri-substituted, independently, with lower alkyl, lower alkoxy, lower alkoxy-substituted lower alkyl, nitro or amino groups, or halogen atoms, and that the description includes both unsubstituted phenyl and naphthyl and substituted phenyl and naphthyl.

The term "q.s." is used herein to mean adding a quantity sufficient to achieve a stated function., for example to bring a solution to a desired volume (q.s. to 100 ml) or to a desired pH (q.s. to pH 4).

It has been discovered unexpectedly that the polyurethanes of the invention are capable of protecting the skin from material that is harmful to the skin, for example toxic chemicals used in the laboratory, industry, in the home, and substances that are capable of penetrating the skin, for example parasites, viruses, bacteria, poisonous gases, toxic agents such as pesticides, herbicides, agents used as chemical weapons, for example mustard gases or neurotoxic agents, and the like.

Accordingly, the present invention relates to a topical composition for protecting the skin of a mammal, comprising: a polyurethane of Formula (I):

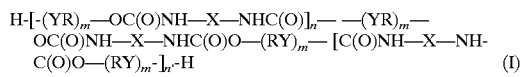

wherein:
X is an alkylene or alkenylene radical containing from 1 to about 20 carbon atoms, or a cycloalkylene or cycloalkenylene radical containing from about 5 to 20 carbon atoms, or a mononuclear or fused ring arylene radical containing from about 6 to about 10 carbon atoms, unsubstituted or substituted with one or more lower alkyl, lower alkoxy, lower alkoxy-substituted lower alkyl, nitro or amino groups or halogen atoms;

Y is oxygen, sulfur or —NR'—, where R' is hydrogen or lower alkyl;

R is the same or different, and is chosen from alkylene, alkenylene, —SiR$^2$R$^3$—, and —CR$^2$R$^3$—NR$^4$—CR$^2$R$^3$—, wherein R$^2$, R$^3$ and R$^4$ are independently hydrogen or lower alkyl;

m is an integer selected to provide a (YR) moiety having a molecular weight of from about 40 to about 10,000; and n' and n are the same or a different integer from 0–30 inclusive, correlated with m so as to provide a polyurethane compound havng a molecular weight of up to about 200,000; and optionally a diluent; in the absence of a phannacologically active agent.

Preferred X groups include:

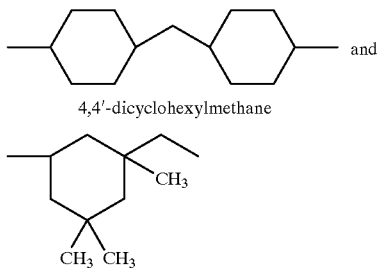

4,4'-dicyclohexylmethane

Preferred Y groups include oxygen and —NR'—.

Preferably when R is an alkylene radical, it contains about 2 to 6 carbon atoms such as —CH$_2$CH$_2$—, —CH$_2$CH$_2$CH$_2$—, —CH$_2$(CH$_3$)—CH$_2$— or —CH$_2$CH$_2$(CH$_3$)—.

Preferably when R is an alkenylene radical, it contains about 1 to 2 double bonds.

Preferably, m is an integer from about 1 to 60.

Preferably n and n' are integers correlated with m so as to provide a polyurethane compound having a molecular weight of about 220 to 200,000, more preferably from about 1000 to 20,000.

Polyurethane compounds of Formula (I) where YR is —SiR$^2$R$^3$— or —CR$^2$R$^3$—NR$^4$—CR$^2$R$^3$— are well known in the art (See for example U.S. Pat. No. 5,286,787 to Padolo and Majolo; U.S. Pat. No. 4,962,178 to Harisiades; Emmons, et. al., U.S. Pat. No. 4,155,892; and "Polyurethanes Chemistry and Technology" by J. H. Saunders and K. C. Frisch, Interscience Publishers, pp. 65–67.)

Also preferred are polyurethanes that are hydroxy-terminated polyurethanes, i.e. where Y is oxygen, especially those where R is alkylene or alkenylene, which are disclosed in U.S. Pat. Nos. 4,971,800, 5,045,317, and 5,051,260, the complete disclosures of which are hereby incorporated by reference. Also useful are those disclosed in Emmons, et al., U.S. Pat. No. 4,079,028, incorporated herein by reference. These references also describe in detail the synthesis of the polyurethane compounds useful in the compositions of the present invention.

A particularly suitable hydroxy-tenminated polyurethane of Formula (I) is of a class of compounds where Y is oxygen, R is an alcylene radical and X is a cycloalkylene radical. In one such polyurethane, X is 4,4'-dicyclohexylmethane, R is 1,2-propylene, m is 12, one of n and n' is 0 and the other is from 1–3, i.e., it is a mixture where one of n and n' is 0 and the other one of n and n' is 1, 2 and 3. It has a tradename of polyolprepolymer-2 ("PP-2"), and is prepared by the reaction of 2 moles of polypropylene glycol and 1 mole of dicyclohexylmethane diisocyanate in the presence of stannous octoate, as detailed in U.S. Pat. No. 4,971,800, Examples 1 and 5. It has a CAS# 9042-82-4, a CAS name of poly[oxy(methyl-1,2-ethanediyl)], $\alpha$-hydro-$\omega$-hydroxy-, polymer with 1,1'-methylene-bis-[4-isocyanatocyclohexane] and a weight average molecular weight of approximately 4000.

In another such polyurethane, X is 4,4'-dicyclohexylmethane, R is 1,2-propylene, m is 51, one of n and n' is 0 and the other is from 1–3. This polyurethane has a tradename of polyolprepolymer-14 ("PP-14"). It has the same CAS# and name as PP-2, but has higher molecular weight (a weight average molecular weight of 18,000 as opposed to 4000 for PP-2).

In yet another such polyurethane, X is 4,4'-dicyclohexylmethane, R is ethylene, m is 8, one of n and n' is 0 and the other is from 1–3. This polyurethane has a tradename of polyolprepolymer-15 ("PP-15"). It has a CAS# 39444-87-6, a CAS name of poly(oxy-1,2-ethanediyl), $\alpha$hydro-$\omega$-hydroxy-, polymer with 1,1'-methylene-bis-[4-isocyanatocyclohexane] and a weight average molecular weight of approximately 1800.

Numerous suitable diluents are known in the art and can be used to formulate the topical composition of the invention. These include, by way of illustration and not limitation, water, and liquid alcohols, glycols, polyethylene glycols, polypropylene glycols, esters, amides, protein hydrolysates, aliylated protein hydrolysates, lanolin, lanolin derivatives, and the like. More typically, suitable diluents are chosen from a mixture of solvents, emollients, humectants, and emulsifiers. Solvents may be water, liquid alcohols, sulfoxides such as dimethylsulfoxide, pyridines, glycols or polyalkylene glycols, such as propylene glycol, butylene glycol, hexylene glycol, polyethylene glycols, and polypropylene glycols. Emollients may be white petrolatum, mineral oil, propylene glycol dicaprylate, lower fatty acid esters and lower alkyl ethers of propylene glycol, cetyl alcohol, cetostearyl alcohol, stearyl alcohol, cetyl esters wax, spermaceti wax, and white wax. Humectants may be glycerin and sorbitol; and emulsifiers may be glyceryl monostearate, glyceryl monooleate, polyoxyethylene cetyl ether, polyoxyethylene cetostearyl ether, polyoxyethylene stearyl ether, and polyethylene glycol stearate. The pH is adjusted where necessary to a pH of about 3.5–7.0, using an acid e.g. hydrochloric acid, phosphoric acid, or a base e.g. diethanolamine, triethanolamine, sodium hydroxide, or known buffering agents, e.g. phosphates such as monobasic sodium phosphate, and dibasic sodium phosphate, and citrates well known in the art. A preservative is generally present, for example benzyl alcohol, sodium benzoate, parabens, and the like.

The invention also relates to a method for protecting the skin of a mammal, in particular that of a human, comprising the application of an effective amount of a polyurethane of Formula (I), optionally combined with a diluent, to the skin of a mammal. Other mammals for which this method and composition are particularly well suited include domestic pets such as cats and dogs, domestic livestock such as cattle, sheep, and pigs, and other mammals such as horses. For example, this invention can be used to protect the skin of a animal from ectoparasites.

The invention further relates to an article of manufacture, comprising a topical composition comprising a polyurethane of Formula (I), and optionally a diluent, in combination with labeling instructions for application of said topical composition for the protection of skin. Such labeling instructions, whether stated on the packaging or in the form of a package insert, would include directions on the amount and frequency of application, methods of removal, suggested storage conditions, shelf life expectancy, any precautions or contraindications that may exist, and so forth.

The amount of polyurethane present in the topical composition of this invention will vary from about 0.1 to about 100 weight percent ("wt %") based upon the total weight of the composition, preferably from about 5 to about 50 wt %.

The topical composition may be formulated as a cream, ointment, gel, lotion, foam, paste, a liquid such as a solution, or other composition which is applied topically. The invention also contemplates compositions in the form of a shampoo that can be applied to the scalp or a soap that can be applied to the hands or other parts of the body, lathered and rinsed to leave a polyurethane coating on the skin. Powders and liquid solutions may also be formulated as aerosols or sprays. Preferably the formulation is a cream, lotion, gel or liquid solution. Typically the composition will be of 10wt % polyurethane in an alcoholic solution, such as a 60/40 water/alcohol solution. Examples of such formulations are shown below.

A cream formulation according to this invention can have the composition shown in Table A, where the polyurethane of Formula (I) is poly[oxy(methyl-1,2-ethanediyl)], $\alpha$-hydro-$\omega$-hydroxy-, polymer with 1,1'-methylene-bis-[4-isocyanatocyclohexane] (PP-2).

TABLE A

| Ingredients | Concentration Wt % | |
|---|---|---|
| | Operable | Preferred |
| Water | qs | qs |
| Glycerin | 2–10 | 5–10 |
| Glyceryl monostearate, self emulsifying type | 1–10 | 2–5 |
| White petrolatum | 1–10 | 4–8 |
| Propylene glycol | 5–20 | 5–15 |
| Propylene glycol dicaprylate | 5–20 | 5–15 |
| Cetyl alcohol | 1–10 | 4–8 |
| Stearic acid | 1–10 | 3–6 |
| PP-2 | 0.1–25 | 15 |
| Polyoxyethylene cetyl ether | 1–10 (n = 20–24) | 2–5 (n = 23) |
| Benzyl alcohol | 0.5–3 | 0.5–1.5 |
| Sodium benzoate | 0–0.5 | 0.2–0.4 |

An acid such as hydrochloric acid or a base such as diethanolamine, triethanolamine (trolamine), potassium hydroxide or sodium hydroxide is used to adjust the pH to between 3.5 to 7.0. Alternatively, a buffering agent such as monobasic or dibasic sodium phosphate with sodium hydroxide or phosphoric acid can be used for pH adjustment. White petrolatum is an emollient cream base and can be replaced by mineral oil. Propylene glycol is a solvent and can be replaced by butylene glycol, hexylene glycol, polyethylene glycols, or polypropylene glycols. Propylene glycol dicaprylate is a solvent/emollient and can be replaced by lower fatty acid esters or lower alkyl ethers of propylene glycol. Glycerin is a humectant/emollient and can be replaced by sorbitol. Glyceryl monostearate, self emulsifying type, is an emulsifier and can be replaced by glyceryl monoleate, self emulsifying type. Polyoxyethylene cetyl ether is an emulsifier and can be replaced by polyoxythylene cetostearyl ether, polyoxythylene stearyl ether, or polyethylene glycol stearates. Cetyl alcohol is an emollient and a emulsion stabilizer/viscosity increasing agent in the cream and can be replaced by cetostearyl alcohol, stearyl alcohol, cetyl esters wax, spermaceti wax or white wax. Sodium benzoate is a preservative and can be replaced by or used in conjunction with benzyl alcohol or parabens, or other commonly used preservatives. Stearic acid is present as an emulsifier and a viscosity enhancer.

Another cream formulation according to this invention can have the composition shown in Table B, where the polyurethane of Formula (I) is PP-2.

TABLE B

| Ingredients | Concentration Wt % | |
|---|---|---|
| | Operable | Preferred |
| Water | qs | qs |
| White petrolatum | 1–20 | 5–10 |
| Propylene glycol | 2–20 | 3–15 |
| Cetearyl alcohol | 1–10 | 3–8 |
| PP–2 | 0.1–25 | 15 |
| Stearic acid | 0–10 | 3–6 |
| Mineral oil | 5–20 | 5–10 |
| Ceteareth-30 | 1–10 | 2–8 |
| Benzyl alcohol | 0.5–3 | 0.5–1.5 |

A buffering agent such as monobasic or dibasic sodium phosphate with sodium hydroxide or phosphoric acid is added to achieve a final pH between 3.5 and 7.0. White petrolatum is an emollient cream base and can be replaced by mineral oil. Propylene glycol is a solvent and can be replaced by butylene glycol or hexylene glycol, polyethylene glycols, polypropylene glycols. Ceteareth-30 is an emulsifying agent and can be replaced by ceteareth-20, steareth-20, or steareth-30.

Another cream formulation according to this invention can have the composition shown in Table C, where the polyurethane of Formula (I) is PP-2.

TABLE C

| Ingredients | Concentration Wt % | |
|---|---|---|
| | Operable | Preferred |
| Water | qs | qs |
| Cetyl alcohol | 1–10 | 2–5 |
| Stearyl alcohol | 1–10 | 2–5 |
| Isopropyl myristate | 1–10 | 5–10 |
| Cetyl palmitate | 1–20 | 1–10 |
| Polysorbate 60 | 1–15 | 1–10 |
| Sorbitan monostearate | 1–15 | 1–10 |
| Stearic acid | 0–10 | 1–6 |
| PP–2 | 0.1–25 | 15 |
| Benzyl alcohol | 0.5–3 | 0.5–1.5 |

An acid such as hydrochloric acid or a base such as diethanolamine, triethanolamine (trolamine), or sodium hydroxide is used to adjust the pH to between 3.5 to 7.0. Isopropyl myristate is a solvent/emollient and isopropyl palmitate may be used in its place. Cetyl palmitate is an emollient and an emulsion stabilizer/ viscosity increasing agent and can be replaced by cetyl esters wax or its various ester components, spermaceti wax, or a white wax. Polysorbate 60 is a hydrophilic nonionic surfactant and is used as an emulsifier. Polysorbate 80 or other suitable polysorbates may be used in its place. Sorbitan monostearate is a lipophilic nonionic surfactant and is used as an emulsifier. Sorbitan palmitate or other sorbitan fatty acid esters may be used in its place.

The cream formulations of Tables A–C are prepared using standard techniques for preparing creams of the oil-in-water emulsion tppe.

A gel formulation according to this invention can have the composition shown in Table D, where the polyurethane of Formula (I) is poly[oxy(methyl-1,2-ethanediyl)], α-hydro-ω-hydroxy-, polymer with 1,1'-methylene-bis-[4-isocyanatocyclohexane] (PP-2).

TABLE D

| Ingredients | Concentration Wt % | |
|---|---|---|
| | Operable | Preferred |
| Water | qs | qs |
| Ethanol | 10–80 | 20–60 |
| Propylene glycol | 3–20 | 5–10 |
| Glycerin | 5–20 | 5–10 |
| PP–2 | 0.1–25 | 15 |
| Hydroxypropyl cellulose | 0.5–3 | 0.5–2 |

An acid such as hydrochloric acid or a base such as diethanolamine, triethanolamine (trolamnine), or sodium hydroxide is used to adjust the pH to between 3.5 to 7.0. Alternatively, buffering agents such as monobasic or dibasic sodium phosphate with sodium hydroxide or phosphoric acid or citric acid in combination with dibasic sodium phosphate can be used to adjust the pH. Isopropyl alcohol can be used in place of ethanol. Propylene glycol is a solvent and can be replaced by butylene glycol, hexylene glycol, polyethylene glycols, or polypropylene glycols. Glycerin is a humectant/emollient and can be replaced by sorbitol. PP-2 can be replaced by polyolprepolymer-14, or polyolprepolymer- 15.

Gels are prepared by the addition of the polyurethanes of the invention to the non-aqueous solvents. If necessary, the base or the buffer (in solution) is added to the above solution with mixing to achieve the desired pH. The hydroxypropyl cellulose is then dispersed into the solution.

An ointment formulation according to this invention can have the composition shown in Table E, where the polyurethane of Formula (I) is PP-2.

TABLE E

| Ingredients | Concentration Wt % | |
|---|---|---|
| | Operable | Preferred |
| White petrolatum | qs | qs |
| Ethanol | 0–20 | 0–5 |
| Propylene glycol | 5–25 | 10–15 |
| PP–2 | 0.1–25 | 15 |
| Glyceryl stearate | 1–8 | 3–5 |

Propylene glycol is a solvent and can be replaced by butylene glycol or hexylene glycol, polyethylene glycols, or polypropylene glycols. Propylene glycol stearate or glyceryl oleate may be used in place of glyceryl stearate as an emulsifier.

The ointment is prepared by mixing the solvents, which are then added to the melted petrolatum and emulsifier with mixing. The preparation is then allowed to cool with continued mixing. Further mixing with a homogenizer may be done.

A lotion formulation according to this invention can have the composition shown in Table F, where the polyurethane of Formula (I) is poly[oxy(methyl-1,2-ethanediyl)], α-hydro-ω-hydroxy-, polymer with 1,1'-methylene-bis-[4-isocyanatocyclohexane] (PP-2).

TABLE F

| Ingredient | Concentration Wt % | |
|---|---|---|
| | Operable | Preferred |
| Water | qs | qs |
| Propylene glycol | 3–20 | 5–10 |
| Glycerin | 2–10 | 3–5 |
| Propylene glycol dicaprylate | 1–15 | 3–10 |
| Glyceryl monostearate, self emulsifying type | 1–5 | 2–3 |
| Polyoxyethylene cetyl ether | 1–5 (n = 20–24) | 2–3 (n = 23) |
| Stearic acid | 1–3 | 1–2 |
| Cetyl alcohol | 0.5–3 | 0.5–2 |
| White petrolatum | 0–5 | 1–2 |
| PP-2 | 0.1–25 | 15 |
| Benzyl alcohol | 0.5–3 | 0.5–1.5 |
| Sodium benzoate | 0–0.5 | 0.2–0.4 |
| Magnesium aluminum silicate | 0.3–1 | 0.5–0.8 |
| Xanthan gum | 0.1–0.5 | 0.2–0.3 |

An acid such as hydrochloric acid or a base such as diethanolamine, triethanolamine (trolamine), or sodium hydroxide is used to adjust the pH to between 3.5 to 7.0. Alternatively, a buffering agent such as monobasic or dibasic sodium phosphate with sodium hydroxide or phosphoric acid can be used for pH adjustment. The materials may be substituted as shown in the cream formulation of Table A.

These lotions are prepared using standard techniques for formulating a lotion of oil-in-water emulsion type. The melted oil phase is added to the aqueous phase in which the thickeners, magnesium aluminum silicate and xanthan gum, are already dispersed. The mixture is then homogenized.

A liquid solution formulation according to this invention can have the composition shown in Table G, where the polyurethane of Formula (I) is PP-2.

TABLE G

| Ingredients | Concentration Wt % | |
|---|---|---|
| | Operable | Preferred |
| Water | qs | qs |
| Ethanol | 10–80 | 20–60 |
| Polyethylene glycol 400 | 5–30 | 5–10 |
| Propylene glycol | 0.1–20 | 5–10 |
| Glycerin | 0–10 | 5–8 |
| PP-2 | 0.1–25 | 15 |

An acid such as hydrochloric acid or a base such as diethanolamine, triethanolamine (trolamine), or sodium hydroxide can be used to adjust the pH to between 3.5 to 7.0. Alternatively, buffering agents such as monobasic or dibasic sodium phosphate with sodium hydroxide or phosphoric acid or a combination of citric acid with dibasic sodium phosphate can be used to adjust the pH. Isopropyl alcohol can be used in place of ethanol. Sorbitol can be used in place of glycerin. PP-2 can be replaced by any polyurethane of the invention, such as polyolprepolymer-14, or polyolprepolymer-15.

These liquid solutions are prepared by addition of the polyolprepolymer to the non-aqueous solvents followed by mixing. If necessary, the base or the buffer (in solution) is added to the above solution with mixing to achieve the desired pH. The liquid solution formulation can be used as a spray as is or as an aerosol with the addition of suitable propellants, for example hydrocarbon gases or low boiling liquids, or standard compressed gases, for example carbon dioxide.

The following Examples serve to illustrate the invention. They are representative in nature and should not be construed in any way as narrowing or limiting the scope of the invention.

EXAMPLE 1

A. A cream having the following composition and containing a polyurethane of Formula (I), e.g., poly[oxy(methyl-1,2-ethanediyl)], α-hydro-ω-hydroxy-, polymer with 1,1'methylene-bis-[4-isocyanatocyclohexane] (PP-2):

| Ingredients | Wt % |
|---|---|
| Water | qs |
| Glycerin | 5 |
| Glyceryl monostearate, self emulsifying type | 3 |
| Triethanolamine | 0.5 |
| White petrolatum | 4 |
| Propylene glycol | 10 |
| Propylene glycol dicaprylate | 5 |
| Cetyl alcohol | 6 |
| Stearic acid | 5 |
| PP-2 | 15 |
| Polyoxyethylene (23) cetyl ether | 4 |
| Benzyl alcohol | 1 |
| Sodium benzoate | 0.2 | is prepared in the following manner:

Into a suitable vessel for holding the water phase, the water is added, followed by the glycerin, triethanolamine, and sodium benzoate with mixing while heating to about 80° C. Into a second vessel suitable for holding the oil phase, a mixture of the white petrolatum, cetyl alcohol, stearic acid, polyoxyethylene (23) cetyl ether, glyceryl monostearate SE, propylene glycol dicaprylate, propylene glycol, and polyolprepolymer-2 are heated to about 80° C. to melt while mixing continuously until uniform. While maintaining the temperature, the oil phase is added to the water phase while mixing. The mixture is cooled to about 50° C. with mixing, then benzyl alcohol is added and mixing continued until uniform. The mixture is then placed under a homogenizer and mixed until smooth and uniform. Mixing is continued with a stirrer at low speed while cooling the mixture to room temperature, giving the desired cream.

B. Similarly, a cream is prepared with the above proportions except that triethanolamine 0.5% is replaced by diethanolamine 0.5%.

Other polyurethanes of Formula (I) can be used in the preparation of the topical formulations of this example.

EXAMPLE 2

A. A cream having the following composition and containing a polyurethane of Formula (I), e.g., poly[oxy(methyl-1,2-ethanediyl)], α-hydro-ω-hydroxy-, polymer with 1,1'methylene-bis-[4-isocyanatocyclohexane] (PP-2):

| Ingredients | Wt % |
|---|---|
| Water | qs |
| Glycerin | 5 |
| Glyceryl monostearate, self emulsifying type | 4 |
| Diethanolamine | 0.3 |
| White petrolatum | 5 |
| Propylene glycol | 7 |

-continued

| Ingredients | Wt % |
| --- | --- |
| Propylene glycol dicaprylate | 7 |
| Cetyl alcohol | 3 |
| Stearic acid | 3 |
| PP-2 | 15 |
| Polyoxyethylene (23) cetyl ether | 2 |
| Benzyl alcohol | 1 |
| Sodium benzoate | 0.2 | is prepared as shown in Example 1.

B. Similarly, a cream is prepared with the above proportions except that diethanolamine 0.3% was replaced by triethanolamine 0.3%.

Other polyurethanes of Formula (I) can be used in the preparation of the topical formulations of this example.

EXAMPLE 3

A. A cream having the following composition and containing a polyurethane of Formula (I), e.g., poly[oxy(methyl-1,2-ethanediyl)], α-hydro-ω-hydroxy-, polymer with 1,1'methylene-bis-[4-isocyanatocyclohexane] (PP-2):

| Ingredients | Wt % |
| --- | --- |
| Water | qs |
| Glycerin | 7 |
| Glyceryl monostearate, self emulsifying type | 4 |
| Triethanolamine | 0.3 |
| White petrolatum | 3 |
| Propylene glycol | 5 |
| Propylene glycol dicaprylate | 7 |
| Cetyl alcohol | 5 |
| Stearic acid | 4 |
| PP-2 | 15 |
| Polyoxyethylene (23) cetyl ether | 3 |
| Benzyl alcohol | 1 |
| Sodium benzoate | 0.2 | is prepared as shown in Example 1.

B. Similarly, a cream is prepared with the above proportions except that triethanolamine 0.3% was replaced by diethanolamine 0.3%.

Other polyurethanes of Formula (I) can be used in the preparation of the topical formulations of this example.

EXAMPLE 4

A cream having the following composition is prepared containing a polyurethane of Formula (I), e.g., poly[oxy(methyl-1,2-ethanediyl)], α-hydro-ω-hydroxy-, polymer with 1,1'-methylene-bis-[4-isocyanatocyclohexane] (PP-2).

| Ingredients | Wt % |
| --- | --- |
| Water | qs to 100% |
| White petrolatum | 8 |
| Propylene glycol | 3 |
| Cetearyl alcohol | 6 |
| PP-2 | 15 |
| Stearic Acid | 4 |
| Mineral oil | 8 |
| Ceteareth-30 | 8 |
| Dibasic sodium phosphate | 0.5 |
| Phosphoric acid | 0.02 |
| Benzyl alcohol | 1 |

The dibasic sodium phosphate is dissolved in the water and phosphoric acid is added. The white petrolatum, cetearyl alcohol, stearic acid, ceteareth-30, mineral oil, polyolrepolymer-2, and propylene glycol are heated to melt with mixing until uniform. The oil phase is then added to the water phase with mixing. The batch is allowed to cool to about 50° C. and benzyl alcohol is added. The batch is homogenized until smooth and uniform and allowed to cool to room temperature with mixing.

Other polyurethanes of Formula (I) can be used in the preparation of the topical formulations of this example.

EXAMPLE 5

A gel having the following composition containing a polyurethane of Formula (I), e.g., poly[oxy(methyl-1,2-ethanediyl)], α-hydro-ω-hydroxy-, polymer with 1,1'-methylene-bis-[4-isocyanatocyclohexane] (PP-2) is prepared.

| Ingredients | Wt % |
| --- | --- |
| Water | qs to 100% |
| Ethanol | 48 |
| Propylene glycol | 10 |
| Glycerin | 5 |
| PP-2 | 15 |
| Hydroxypropyl cellulose | 1.8 |

The polyethylene glycol 400, propylene glycol, glycerin, and polyolprepolymer-2 are added to the ethanol and mixed until uniform. Water is then added and mixed until uniform. If necessary, the base or the buffer (in solution) is added to the above solution with mixing to achieve the desired pH. The hydroxypropyl cellulose is then dispersed into the solution.

Other polyurethanes of Formula (I) can be used in the preparation of the topical formulations of this example.

EXAMPLE 6

A lotion having the following composition and containing a polyurethane of Formula (I), e.g., poly[oxy(methyl-1,2-ethanediyl)], α-hydro-ω-hydroxy-, polymer with 1,1'-methylene-bis[4-isocyanatocyclohexane] (PP-2) is prepared.

| Ingredients | Wt % |
| --- | --- |
| Water | qs to 100% |
| Propylene glycol | 3 |
| Glycerin | 5 |
| Propylene glycol dicaprylate | 3 |
| Glyceryl monostearate, self emulsifying type | 2 |
| Polyoxyethylene cetyl ether | 2 |
| Stearic acid | 2 |
| Cetyl alcohol | 0.5 |
| White petrolatum | 1 |
| PP-2 | 15 |
| Benzyl alcohol | 1 |
| Sodium benzoate | 0.2 |
| Magnesium aluminum silicate | 0.4 |
| Xanthan gum | 0.25 |
| Triethanolamine | 0.3 |

Mix the magnesium aluminum silicate and xanthan gum and disperse into the water using a homogenizer. Add the glycerin to the above water phase and heat to 70 to 80° C. with mixing. Into another vessel for holding the oil phase, add the propylene glycol dicaprylate, propylene glycol, glyceryl monostearate SE, cetyl alcohol, white petrolatum, stearic acid, polyoxyethylene (23) cetyl ether, polyolprepolymer-2. Heat to 70 to 80° C. with mixing until melted and uniform. Add the oil phase to the water phase with mixing. Dissolve the triethanolamine and sodium benzoate in the remaining water and add to the batch with mixing. Cool the batch to about 50° C. and add the benzyl alcohol. Homogenize the batch and then allow to cool to room temperature with mixing.

Other polyurethanes of Formula (I) can be used in the preparation of the topical formulations of this example.

EXAMPLE 7

A liquid solution containing a polyurethane of Formula (I), e.g., poly[oxy(methyl-1,2-ethanediyl)], α-hydro-ω-hydroxy-, polymer with 1,1'-methylene-bis-[4-isocyanatocyclohexane] (PP-2) and having the following composition is prepared.

| Ingredients | Wt % |
| --- | --- |
| Water | qs to 100% |
| Ethanol | 48 |
| Polyethylene glycol 400 | 5 |
| Propylene glycol | 10 |
| Glycerin | 5 |
| PP-2 | 15 |

The polyethylene glycol 400, propylene glycol, glycerin, and polyolprepolymer-2 are added to the ethanol and mixed until dissolved and uniform. Water is added, and mixed until uniform. The pH of the solution is 4.4. Triethanolamine (TEA) can be added to further increase the pH if necessary. For example, 0.05 g of TEA in 100 g of solution would bring the pH to 5.1 whereas 0.1 g of TEA would give a pH of 5.6.

Other polyurethanes of Formula (I) can be used in the preparation of the topical formulations of this example.

EXAMPLE 8

Prevention of Cutaneous Irritation

Prevention of cutaneous irritation was measured in a blinded experiment to determine whether the polyurethanes of the invention could reduce skin irritation caused by high alkaline (NaOH) content hair relaxers. The hair relaxer used in the study was the Bone Strength Relaxer System, regular strength, manufactured by Alberto-Culver. The hair relaxer was tested alone ("control") or in combination with 10% (v/v) poly[oxy(methyl-1,2-ethanediyl)], α-hydro-ω-hydroxy-, polymer with 1,1'-methylene-bis-[4-isocyanatocyclohexane] ("PP-2") or 10% (v/v) poly(oxy-1,2-ethanediyl), αhydro-ω-hydroxy-, polymer with 1,1'-methylene-bis-[4-isocyanatocyclohexane] ("PP-15").

Three 1 cm$^2$ dose areas of the skin were demarcated on the previously non-exposed ventral forearm skin of each of three human volunteers (Subjects 1, 2 and 3, respectively). Each site was labeled as A, B or C, and 5 μL of the respective formulation was applied to the site using a positive displacement syringe. After about 5 minutes ("exposure time"), each site was washed with cold water with liquid soap and then rinsed with cold running tap water. Changes in skin irritation were recorded over a 24 hour period using a scale of 0–7, with 0 being no evidence of irritation and 7 indicating a strong reaction spreading beyond the test site. The experiment was subsequently repeated with a 10 minute exposure time and a 15 minute exposure time.

Overall, no reactions were noted on two subjects, while one subject had a slight reaction at site B, with no reaction at sites A and C. The experiment was unblinded to show the following:

TABLE 1

| Site | Formulation |
| --- | --- |
| A | hair relaxer (regular strength) + 10% (v/v) PP-15 |
| B | hair relaxer (regular strength) |
| C | hair relaxer (regular strength) + 10% (v/v) PP-2 |

This experiment was repeated using the super strength formulation of the Bone Strength Relaxer System. Overall, no reactions were noted by the subjects, except for a slight reaction at site C. The experiment was unblinded to show the following:

TABLE 2

| Site | Formulation |
| --- | --- |
| A | hair relaxer (super strength) + 10% (v/v) PP-15 |
| B | hair relaxer (super strength) + 10% (v/v) PP-2 |
| C | hair relaxer (super strength) |

These experiments show that PP-2 and PP-15 have the ability to decrease NaOH induced skin irritation.

EXAMPLE 9

Determination of Skin Barrier Properties Against Parasites

Infection by schistosome cercariae occurs by penetration of intact skin by aquatic cercariae. Skin penetration by these parasites is facilitated by a serine protease secreted by the cercariae in response to skin lipids. See Stirewalt, et al., *Exp. Parasitol* 35:1–15 (1974) and McKerrow, et al., *Proc. Soc. Exp. Biol. Med.* 197:119–124 (1991).

In this experiment, the details of which are described in greater detail in Lim, et al., *Amer. Jour. Tropical Medicine & Hygiene* 60 (3): 487–492 (1999) several topical carriers are evaluated for their ability to block cercarial invasion. Polyurethane-containing as well as non-polyurethane-containing formulations were also evaluated with and without the addition of a peptide protease inhibitor.

The Puerto Rican strain of *Schistosoma mansoni* was used. Details of the maintenance and collection of cercariae from infected snails is set forth in Lim, et al., *Adv. Parasitol* 10:191–268 (1972) and McKerrow, et al., *J. Biol. Chem.* 260:3703–3707 (1985). Cercariae were used for skin penetration experiments immediately after shedding from snails. The tetrapeptide protease inhibitor Suc-Ala-Ala-pro-Phe-CK, was obtained from Enzyme Systems Products (Dublin, Calif.).

The topical formulations were first prepared as inhibitor in a 50% dimethylsulfoxide ("DMSO")/water (v/v) stock solutions, followed by the addition of 10% (v/v) polyolprepolymer.

In vitro invasion assay using human skin

Lower extremity or abdominal human skin samples were harvested from autopsy or surgical pathology specimens. After removal of subcutaneous fat, the skin was placed between two plastic chambers or in strips over wells of a 24-well tissue culture dish. Tissue culture media (RPMI-1640) was added to the wells beneath the skin and warmed to 37° C. to crate a thermal gradient. Three thousand cercariae in water were introduced into the upper chamber. Formulations to be evaluated were placed on the skin surface. The DMSO solvent was allowed to evaporate for 30 min. before application of cercariae.

Following introduction of cercariae, the plates were incubated for 2 hrs., the cercariae removed, and the skin cut into 1 mm strips and fixed in 10% phosphate buffered formalin. Following routine paraffin embedding, the histologic sections were prepared and stained with hematoxylin and eosin to identify organisms that had penetrated the skin.

TABLE 3

| Formulation | # Larva Penetrating Skin (mean ± SD) |
|---|---|
| Water | 56 ± 17 |
| PP-14 | 18 ± 16 |
| PP-14 + inhibitor | 3 ± 3 |
| PP-15 | 2 ± 2 |
| PP-15 + inhibitor | 1 ± 2 |
| PP-2 | 0 ± 0 |
| PP-2 + inhibitor | 0 ± 0 |

Assay of worm burden and egg burden in mice exposed to cercariae with and without inhibitors PP-2, with and without inhibitor, was applied to the tails of seven-week-old balb/c mice. Mice were then exposed to 120 cercariae by tail immersion for 30 min. Seven weeks later, the mice were euthanized and worm burden and egg burden determined as described by Amiri, et al., *Nature* 356:604–607 (1992). Adult worms were perfused from the liver and counted, and the liver tissue was digested with 0.7% trypsiniphosphate buffered saline to release eggs, which were counted in a hemocytometer. Egg burden was calculated per gram of liver tissue.

TABLE 4

| Formulation | Number of Worms Per Mouse | Mean ± SD |
|---|---|---|
| Untreated (control) | 8–29 | 15 ± 7 |
| PP-2 | 1–21 | 8 ± 8 |
| PP-2 + inhibitor | 0–11 | 4 ± 4 |

TABLE 5

| Formulation | Number of Eggs Per Gram of Liver Tissue (mean ± SD) |
|---|---|
| Untreated (control) | 1224 ± 796 |
| PP-2 | 425 ± 429 |
| PP-2 + inhibitor | 91 ± 131 |

As can be seen in Tables 4 and 5, the number of worms per mouse decreased from 8–29 in untreated animals to 1–21 in formulations containing PP-2 alone. Similarly, egg burden decreased from a mean of 1224 in controls to 425 in PP-2 alone.

EXAMPLE 10

Method of Determining Depth of Polvurethane Skin Deposition

The use of Fourier Transform Infrared spectrometers equipped with the attenuated total reflectance ("FTIR-ATR") has been shown to be a useful non-invasive method of studying the biophysical properties of skin. This technique has recently been used to study the barrier fumction of the stratum corneum (Bommannan, et al., in *Jour. of Investigative Dermatology* 95:403–408 (1990) and in *Jour. of Investigative Dermatology* 92:405 (1989)), the water content of stratum corneum (Edwardson, et al., *Jour. of Pharmaceutical & Biomedical Analysis* 9:1089–1094 (1991) and Potts, et al., *Archives of Dermatological Research* 277:489–495 (1985)), the effect of the permeation enhancer oleic acid on the stratum comeum (Mak, et al., *Jour. of Controlled Release* 12:67–75 (1990)), and the distribution of cyanophenol in the stratum corneum (Higo, et al., *Intern. Symp. Control. Rel. Bioact. Mater.* 17:413 (1990)).

In this example, the FTIR-ATR technique was used to assess the presence and amount of polyolprepolymer-2 ("PP-2") in the stratum corneum of two human subjects, in vivo. The feasibility of FTIR-ATR in quantifying the amount of PP-2 in stratum corneum was confirmed by the results from in vitro uptake studies and in vivo occlusive and non-occlusive studies performed with radiolabeled PP-2.

FTIR-ATR (in vivo)

The test solution contained 10 wt % PP-2 dissolved in ethanol/water (60:40 v/v). the control solution consisted only of ethanol/water (60:40 v/v). Webtril™ pads (12cm× 2.5cm) were saturated either with test or control solution and were applied to the left and right forearms of two subjects, respectively. The pads were secured in place with Tegaderm 1626™ occlusive transparent dressing during the entire 3 hour exposure period. The skin surface of the dosing sites was lightly wiped with two cotton-tipped swabs following the exposure period. A total of 8 tape strippings were performed: 6 were done immediately and 2 were done 2 hours later. FTIR spectra of the dosing sites were obtained prior to tape stripping and subsequently after each tape strip using the FTIR-ATR Nicolet 520) equipped with a 7.2 cm$^2$ ZnSe crystal. FTIR spectrum of PP-2 at a known surface concentration was obtained with 30 $\mu$L of test solution (specific gravity of 0.902 g/mL).

FTIR spectra of the stratum comeum was measured from the dosing site and compared with the FTIR spectra of PP-2. The ratio of PP-2 absorption at 1095 cm$^{-1}$ to stratum corneum absorption at 675 cm$^{-1}$ (R 1095/675) was determined to account for potential differences in degree of contact between the sample (forearm) and the ATR crystal. In addition, the difference in the ratios between the treated and control sites (R 1095/675 treated and R 1095/675 control) was obtained to determine the skin surface concentration of PP-2.

The absorbance ratio, R 1095/675, of PP-2 was determined. The quantity $\epsilon$b was computed, based upon the known surface concentration of PP-2 and using Beer's Law (A=$\epsilon$bC). Finally, the skin surface concentration of PP-2 was estimated using R 1095/675 and $\epsilon$b values. PP-2 was found to be in the range of 13–17 $\mu$g/cm$^2$ of stratum corneum.

Occlusive and Non-occlusive (in vivo)

The test solution contained ~0.1 $\mu$Ci$^3$H-polyurethane oligomers/mg PP-2. Approximately 15 mg of the test solution was applied to the left ventral forearms of two subjects. Thereafter, the occlusive (absent the Webtril™ pad) or non-occlusive (Bucks, et al., *Pharm. Res.* 5:313–315 (1988)) chamber was placed over the site of the application for the entire 24 hour exposure period. Radiolabel dose accountability was assessed from the chamber wash, skin wash, tape strips, and urine samples by liquid scintillation counting (Packard 1900CA).

Of the applied doses, the mean radiolabel ($^3$H-polyurethane oligomers) recovered was 95% from the occlusive study and 93% from the non-occlusive study. In mass, 3–7 and 4–7 μg polyurethane oligomers/cm² of stratum corneum was recovered from the occlusive and non-occlusive studies, respectively.

Uptake studies (in vitro)

The test solution contained ~0.9 μCi³H-PP-2/mg PP-2 dissolved in 2.5 mL of 40% ethanol in water for the measurement of uptake of ³H-PP-2 from a solution of 1% PP-2 in 40% ethanol in water as well as the measurement of uptake of unlabeled PP-2 by weight. Human stratum comeum sheets (~0.3 mg for labeled and ~50 mg for unlabeled) were prepared as described in Golden, et al., *Jour. of Investigative Dermatology* 86:255–259 (1986), and were treated with the test solution for 2 hours. Following treatment, the sheets were treated with labeled PP-2, rinsed with cold ethanol, digested with KOH, neutralized with HCl, and assayed for radioactivity by liquid scintillation counting. The sheets that were treated with unlabeled PP-2 were rinsed with cold ethanol, exposed to ambient conditions for 3 days followed by storage at constant relative humidity in a dessicator. Weights before and after the treatment period were recorded.

Based upon the activity of ³H-PP-2 in stratum corneum and the weight change of the stratum corneum following PP-2 treatment, the uptake of PP-2 was determined to range from 30–48 and 10–26 μg/cm² of stratum comeum, respectively.

TABLE 6

| Study | Concentration (μg/cm²) | Range | Mean ± SD |
|---|---|---|---|
| FTIR-ATR (in vivo) | 13–17 | 2 | |
| Occlusive (in vivo) | 4–9* | 2 | |
| Non-occlusive (in vivo) | 5–9* | 2 | |
| Uptake by Weight Change (in vitro) | 10–26 | 2 | |
| Uptake by Radioactivity (in vitro) | 30–48 | 3 | 41 ± 10 |

*These values were estimated based upon 20% polypropylene glycol in PP-2. Occlusive and non-occlusive studies utilize vigorous skin washing that would lower PP-2 skin levels more so than light, dry wiping from the FTIR-ATR study and no wiping in the uptake studies.

This example shows that PP-2 is localized in the stratum corneum. In addition, because the results form the FUR studies were within the magnitude of the results of the occlusive, non-occlusive and uptake studies, it is established that FTIR-ATR is feasible in detecting and quantitating PP-2 in human stratum corneum in vivo.

A total of 5 successive tape strippings were required to remove sebaceous lipids from the stratum corneum utilizing the FnR-AfR as described by Bommannan, et al., Supra (1990). PP-2 is perhaps localized in stratum corneum by a mechanism similar to that for the localization of sebaceous lipids.

EXAMPLE 11

Determination of Skin Barrier Properties Against Herbicides

The barrier properties of two different polyurethanes were studied for their ability to inhibit penetration of the commercial herbicide AAtrex 4L (Novartis), which contains 41% atrazine. The hydrophobic polyurethane, poly[oxy (methyl-1,2-ethanediyl)], α-hydro-ω-hydroxy-, polymer with 1,1'-methylene-bis-[4-isocyanatocyclohexane] or polyolprepolymer-2 ("PP-2"), and the hydrophilic polyurethane, poly(oxy-1,2-ethanediyl), α-hydro-ω-hydroxy-, polymer with 1,1'-methylene-bis-[4-isocyanatocyclohexane] or polyolprepolymer- 15 ("PP-15") were chosen for evaluation.

Excised hairless mouse skin (CRL:SKH1) was placed in a flow-through cell diffusion system. The polyurethanes were diluted to 10, 20 and 30% (v/v) strength with ethanol. Ten microliters of each polyurethane solution was then placed on the epidermis and equilibrated for one hour. AAtrex 4L was diluted 1:40 (v/v) with water giving a concentration similar to that typically used in the agricultural industry. One hundred microliters of this solution, spiked with ¹⁴C labeled atrazine were then placed on pretreated skin. Atrazine penetration (unoccluded) was determined in 90-minute increments over a 24-hour exposure period.

The amount of atrazine penetrating through the skin was reduced by 70, 64 and 40 percent for the 30,20 and 10 percent PP-2 (v/v) formulations, respectively. PP-15, although less effective, still significantly reduced atrazine penetration, exhibiting 53, 39 and 21 percent reduction for the 30, 20 and 10 percent (v/v) formulations, respectively.

This work showed that the polyurethanes of the invention are effective at reducing the quantity of the atrazine-containing herbicide AAtrex 4L that is able to penetrate the skin.

EXAMPLE 12

Determination of Skin Barrier Properties Against 5-Fluorouracil

The barrier properties of two. different polyurethanes were studied for their ability to inhibit penetration of 5-fluorouracil ("5-FU"). The hydrophobic polyurethane, PP-2, and the hydrophilic polyurethane, PP-15 were chosen for the study.

Dermatomed human cadaver skin (n=6) mounted on flow-trough diffusion cells were pretreated over a 0.64 cm² surface are with 10.0 μL of solvent alone or 10% (v/v) polymer in solvent using a micropipettor. The dermis was perfused overnight (approximately 20 hours) with phosphate-buffered saline at pH 7.4 containing 0.1% sodium azide and 1.5% oleth 20 at 1 mL/hour at 37° C. At the end of pretreatment, the skin was double wiped consecutively with wash solution (1% sodium laurel sulfate, 1% aluminum laurel sulfate in water) soaked swabs, followed by two repetitive water swabs, and wiped dry with a single swab. The swabs were discarded. The skin was then dosed with 150 μL of saturated aqueous 5-FU (10.2 mg/mL at 32 ±1° C.) at a concentration sufficient to achieve an approximately 2.0μCi ³H 5-FU dose. The receptor phase was then collected every 6 hours for 24 hours.

TABLE 7

| Formulation | % Dose Penetrating Skin (mean ± SD) | % Inhibition |
|---|---|---|
| Methylene chloride | 0.27 ± 0.20 | — |
| Methylene chloride + 10% PP–2 | 0.21 ± 0.05 | 22% |
| Methylene chloride + 10% PP–15 | 0.15 ± 0.10 | 44% |
| Ethanol | 0.15 ± 0.08 | — |
| Ethanol + 10% PP–2 | 0.11 ± 0.05 | 27% |
| Ethanol + 10% PP–15 | 0.09 ± 0.04 | 40% |

This study showed that skin pre-treatment with polyurethanes of the invention are effective at reducing the quantity of 5-FU that is able to penetrate the skin.

EXAMPLE 13

Determination of Skin Barrier Properties Against Toxic Chemicals

The barrier properties of three different polyurethanes were studied for their ability to inhibit penetration of two highly toxic chemical warfare agents, radiolabeled for purposes of evaluation. [1,3-$^{14}$C] diisopropylfluorophosphate ("DFP"), specific activity of 160 mCi/mmole and a reported radiochemical purity of 99% was obtained from DuPont-NEN (Wilmington, Del.), and was diluted with diisopropylfluorophosphate (Sigma Chemical Company, St. Louis, Mo.) to a specific activity of approximately 0.07 $\mu$Ci/$\mu$L. n-Butyl-[1,2-$^{14}$C] 2-chloroethylsulfide ("NBCS"), specific activity of 10.97 mCi/mmole and a radiochemical purity of 92% was obtained from ICN (Irvine, Calif.), and was diluted with n-butyl-2-chloroethylsulfide (Columbia Organic Chemical Co., Columbia, S.C.) to a specific activity of approximately 1 $\mu$Ci/$\mu$L. The polyurethanes, PP-2, PP-14 and PP-15 were chosen for the study. The formulations were all q.s. to 5.0 ml with 75% (w/w) ethanol. The control formulation was an ethanol, propylene glycol, water mixture.

Silastic membrane (0.1 mm thick) was cut into circles and mounted on difflusion cells. The cells were maintained at 37° C. Each membrane was dosed with 10 $\mu$L of test or control formulation, spread onto the membrane with a glass rod or placed as a droplet on the membrane surface. The treatments were challenged with 1 $\mu$L (0.00573 mmole) of C$^{14}$-labeled DFP or C$^{14}$-labeled NBCS). The donor chamber was closed and a peristaltic pump caused tissue culture medium (Roswell Park Memorial Institute formula 1640, Sigma) to flow underneath the silastic membranes for 4 hours at 1 ml/hr. The flow was fractionated into hourly samples, which were weighed and the radioactivity counted. After the four hour period, the diffusion cell was disassembled and the silastic membrane removed and placed in a vial and its radioactivity measured.

TABLE 8

| Formulation | % dose Penetrating Silastic Membrane (mean ± SD) | |
| --- | --- | --- |
|  | DFP | NBCS |
| Control | 60 ± 5 | 26 ± 3 |
| PP-2 | 60 ± 5 | 20.6 ± 0.5 |
| PP-14 | 60 ± 8 | 20 ± 2 |
| PP-15 | 58 ± 3 | 22.3 ± 0.5 |

Penetration of DFP was slightly inhibited by PP-15. PP-2, PP-14 and PP-14 were all able to inhibit penetration of NBCS.

This study showed that pretreatment of the test membrane with the polyurethanes of the invention resulted in a decrease in penetration by the toxic agents.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

We claim:
1. A method for protecting the skin of a mamnmal, comprising applying to the skin of a mammal an effective amount of a polyurethane of Formula (I) in the absence of a pharmacologically active agent:

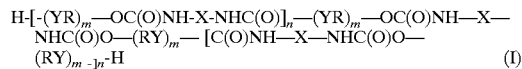

H-[-(YR)$_m$—OC(O)NH-X-NHC(O)]$_n$—(YR)$_m$—OC(O)NH—X—NHC(O)O—(RY)$_m$— [C(O)NH—X—NHC(O)O—(RY)$_{m\,-]_{n'}}$-H      (I)

wherein:
X is an alkylene or alkenylene radical containing from 1 to about 20 carbon atoms, or a cycloalkylene or cycloalkenylene radical containing from about 5 to 20 carbon atoms, or a mononuclear or fused ring arylene radical containing from about 6 to about 10 carbon atoms, unsubstituted or substituted with one or more lower alkyl, lower alkoxy, lower alkoxy-substituted lower alkyl, nitro or amino groups or halogen atoms;

Y is oxygen, sulfur or —NR'—, where R' is hydrogen or lower alkyl;

R is the same or different, and is chosen from alkylene, alkenylene, —SiR$^2$R$^3$—, and —CR$^2$R$^3$NR$^4$—CR$^2$R$^3$ —, wherein R$^2$, R$^3$ and R$^4$ are independently hydrogen or lower alkyl;

m is an integer selected to provide a (YR) moiety having a molecular weight of from about 40 to about 10,000; and n and n' are the same or a different integer from 0–30 inclusive, correlated with m so as to provide a polyurethane compound having a molecular weight of up to about 200,000;

wherein said polyurethane forms a barrier on the surface of the skin and is absorbed into the outer layer of the skin.

2. The method of claim 1 wherein said polyurethane is combined with a diluent.

3. The method of claim 2 wherein said diluent is a solvent, emollient, humectant or emulsifier.

4. The method of claim 1, wherein the polyurethane is applied as a cream, ointment, gel, lotion, foam, aerosol, spray, or liquid.

5. The method of claim 4, wherein the composition is a liquid.

6. The method of claim 5, wherein the composition further comprises an alcohol.

7. The method of claim 1, wherein Y is oxygen, X is a cycloalkylene radical and R is alkylene.

8. The method of claim 7, wherein X is 4,4'-dicyclohexylmethane and R is 1,2-propylene.

9. The method of claim 8, wherein m is 12, and one of n and n' is 0 and the other one of n and n' is from 1–3.

10. The method of claim 8, wherein m is 51, and one of n and n' is 0 and the other one of n and n' is from 1–3.

11. The method of claim 9, wherein X is 4,4'-dicyclohexylmethane and R is ethylene.

12. The method of claim 11, wherein m is 8, and one of n and n' is 0 and the other one of n and n' is from 1–3.

13. The method of claim 1 wherein the polyurethane of Formula (I) is selected from the group consisting of poly [oxy(methyl-1,2-ethanediyl)], $\alpha$-hydro-$\omega$-hydroxy-, polymer with 1,1'methylene-bis-[4-isocyanatocyclohexane] and having a molecular weight of 4000; poly[oxy(methyl-1,2-ethanediyl)], $\alpha$-hydro-$\omega$-hydroxy-, polymer with 1,1'-methylene-bis-[4-isocyanatocyclohexane] and having a molecular weight of 14,000; and poly(oxy-1,2-ethanediyl), $\alpha$hydro-$\omega$-hydroxy-, polymer with 1,1'-methylene-bis-[4-isocyanatocyclohexane].

14. The method of claim 1, wherein X is

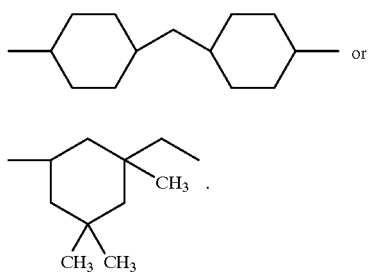

or

15. The method of claim 1, wherein Y is oxygen or —NR'—.

16. The method of claim 1, wherein R is an alkylene radical containing about 2 to 6 carbon atoms.

17. The method claim 16 wherein R is —CH$_2$CH$_2$—, —CH$_2$CH$_2$CH$_2$—, —CH$_2$(CH$_3$)—CH$_2$— or —CH$_2$CH$_2$(CH$_3$)—.

18. The method of claim 1, wherein R is an alkenylene radical containing about 1 to 2 double bonds.

19. The method of claim 1, wherein m is an integer from about 1 to 60.

20. The method of claim 1, wherein n and n are correlated with m so as to provide a polyurethane compound having a molecular weight of about 220 to 200,000.

21. The method of claim 20, wherein n and n are correlated with m so as to provide a polyurethane compound having a molecular weight of about 1000 to 20,000.

* * * * *